United States Patent

Fukuda

(10) Patent No.: US 9,459,150 B2
(45) Date of Patent: Oct. 4, 2016

(54) FOURIER TRANSFORM INFRARED SPECTROPHOTOMETER

(71) Applicant: SHIMADZU CORPORATION, Kyoto-shi, Kyoto (JP)

(72) Inventor: Hisato Fukuda, Muko (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/770,849

(22) PCT Filed: Feb. 28, 2013

(86) PCT No.: PCT/JP2013/055295
§ 371 (c)(1),
(2) Date: Aug. 27, 2015

(87) PCT Pub. No.: WO2014/132379
PCT Pub. Date: Sep. 4, 2014

(65) Prior Publication Data
US 2016/0003676 A1    Jan. 7, 2016

(51) Int. Cl.
*G01J 5/02*    (2006.01)
*G01J 3/453*    (2006.01)
*G01J 3/02*    (2006.01)
*G01N 21/35*    (2014.01)
*G01J 3/10*    (2006.01)
*G01J 3/12*    (2006.01)

(52) U.S. Cl.
CPC .............. *G01J 3/4535* (2013.01); *G01J 3/027* (2013.01); *G01J 3/0264* (2013.01); *G01J 3/0275* (2013.01); *G01J 3/0289* (2013.01); *G01J 3/108* (2013.01); *G01J 3/12* (2013.01); *G01N 21/35* (2013.01); *G01N 2021/3595* (2013.01)

(58) Field of Classification Search
CPC ................ G01N 2021/3595; G01N 2021/024
See application file for complete search history.

(56) References Cited

U.S. PATENT DOCUMENTS

| 4,473,295 A * | 9/1984 | Doyle ................... G01N 21/474 356/244 |
| 5,153,675 A * | 10/1992 | Beauchaine ............ G01J 3/453 250/339.08 |
| 2013/0003060 A1* | 1/2013 | Kimura ..................... G01J 3/08 356/319 |

FOREIGN PATENT DOCUMENTS

| EP | 1376050 A2 | 1/2004 |
| JP | 2-253103 A | 10/1990 |
| JP | 5-87634 A | 4/1993 |
| JP | 2005-241551 A | 9/2005 |
| WO | 2012/056776 A1 | 5/2012 |

OTHER PUBLICATIONS

International Search Report for PCT/JP2013/055295 dated Mar. 26, 2013.
International Written Opinion for PCT/JP2013/055295 dated Mar. 26, 2013 [PCT/ISA/237].
Communication dated Feb. 1, 2016, issued by the European Patent Office in corresponding European Application No. 13876680.3.

* cited by examiner

Primary Examiner — Kiho Kim
(74) Attorney, Agent, or Firm — Sughrue Mion, PLLC

(57) ABSTRACT

A Fourier transform infrared spectrophotometer that is free from an effect of interference condition change resulting from an accessory being mounted and has a high measurement accuracy is provided. A Fourier transform infrared spectrophotometer according to the present invention is a Fourier transform infrared spectrophotometer including a common base on which a sample chamber 2 and an interference optical system are mounted, where an accessory 20 can be detachably in the sample chamber, the Fourier transform infrared spectrophotometer including: accessory information reading means 22 for reading accessory information provided to the accessory 20 when the accessory 20 is mounted in the sample chamber 2; and setting condition changing means (controller 30) for changing a setting condition for the interference optical system based on the accessory information read by the accessory information reading means 22, the setting condition varying depending on, e.g., a difference in weight between respective accessories 20.

4 Claims, 4 Drawing Sheets

FOURIER TRANSFORM INFRARED SPECTROPHOTOMETER

CROSS REFERENCE TO RELATED APPLICATIONS

This application is a National Stage of International Application No. PCT/JP2013/055295 filed Feb. 28, 2013, the contents of which are incorporated herein by reference in their entirety.

TECHNICAL FIELD

The present invention relates to a Fourier transform infrared spectrophotometer (hereinafter, "FTIR").

BACKGROUND ART

In the FTIR, an infrared interference wave whose amplitude oscillates is generated by an interferometer, such as a Michelson interferometer, and is cast to a sample. Light transmitted by the sample or light reflected by the sample is detected as an interferogram, and the interferogram is subjected to Fourier transformation to obtain a spectrum (power spectrum) with the wavenumber as the abscissa and the intensity as the ordinate. Here, the Michelson interferometer is a device including a beam splitter (half mirror), a fixed mirror, a moving mirror. Light is divided into two light beams by the beam splitter, one of the light beams is reflected by the fixed mirror while the other light beam is reflected by the moving mirror, and then these two reflected light beams are made to interfere with each other. The amplitude of the resulting interference light oscillates with time as a result of moving the moving mirror.

The power spectrum obtained from light transmitted or reflected by a sample as described above is referred to as "sample spectrum" in the present description. Since a sample spectrum contains a background, it is necessary to subtract the background from the sample spectrum in order to obtain an absorption spectrum or a transmission spectrum. For that subtraction, conventionally, in the FTIR, a measurement is performed without sample before sample spectrum measurement to obtain a spectrum of the background.

If the direction of the moving mirror changes (if the moving mirror pitches or yaws) while a sample spectrum and a background spectrum are measured, temporal fluctuations may occur in the amplitude of the resulting infrared interference wave. Therefore, in the FTIR, in order to prevent fluctuations in the amplitude of the infrared interference wave due to change in the direction of the moving mirror, dynamic alignment is widely used (Patent Literature 1).

In dynamic alignment, laser light with a cross-sectional area smaller than that of infrared light to be used to obtain an interferogram in a main interferometer (Michelson interferometer) is used to perform a preliminary measurement for measuring change in the direction of the moving mirror while in motion. The preliminary measurement is made by detecting, with a photodiode array, movement of the position of a spot of the laser light during movement of the moving mirror with no sample provided. Based on a result of the preliminary measurement, when an FTIR measurement is performed, the direction of the fixed mirror is continuously adjusted during movement of the moving mirror so as to cancel out the effect of the change in the direction of the moving mirror. The adjustment of the direction of the fixed mirror is made by, for example, applying a voltage to a piezoelectric element provided on the back of the fixed mirror.

CITATION LIST

Patent Literature

[Patent Literature 1] JP 02-253103A

SUMMARY OF INVENTION

Technical Problem

In the FTIR, a replaceable measurement accessory is mounted in a sample chamber in which a sample is to be set, depending on the relevant measurement method such as an attenuated total reflection (ATR) measurement method, a specular reflection measurement method or a diffuse reflection measurement method, or depending on the state (gas, liquid or solid) of the sample. For example, for measuring a liquid or a gas, an accessory including a cell that contains the liquid or the gas is used. Also, for performing an ATR measurement, an accessory equipped with a movement mechanism that presses a sample to a surface of a prism and moves the prism in order to change an angle of infrared interference light incident on the sample is used. Examples of the movement mechanism include ones using a motor as well as manual ones. Also, an infrared microscope may be mounted in the sample chamber as an accessory.

The sample chamber in which these accessories are mounted is placed on an device chassis via a suspension so that vibration is hardly transmitted to the sample chamber; however, when the interference conditions are adjusted to be optimum with no accessory mounted in the sample chamber, the interference conditions deviate from the optimum interference conditions as a result of an accessory being mounted, and the deviation differs depending on the accessory.

A decrease in signal intensity due to such interference condition deviation causes a decrease in measurement accuracy of the FTIR even if dynamic alignment is performed. An object of the present invention is to provide an FTIR that is free from an effect of interference condition deviation resulting from an accessory being mounted and has a high measurement accuracy.

Solution to Problem

The present inventor has found that a cause of interference condition deviation resulting from an accessory being mounted lies in that a base on which a sample chamber and an interferometer are installed via respectively provided independent suspensions is slightly distorted by the weight of the accessory. Distortion of the base changes a mutual positional relationship between a fixed mirror and a moving mirror in the interferometer. The interference conditions sensitively change depending on the positional relationship, and thus, even slight distortion of the base may cause an adverse effect. Also, distortion of the base may cause displacement of an incident position of infrared light on a detector.

Furthermore, optical elements, such as prisms, mirrors and/or slits, included in an optical path or an accessory are different depending on the accessory, and the throughput is thus different. Therefore, the amount of infrared light entering a detector decreases, which may result in decrease in signal intensity.

The present invention made in order to solve the aforementioned problem provides a Fourier transform infrared spectrophotometer including a common base on which a sample chamber and an interference optical system are mounted, where an accessory can be detachably installed in the sample chamber, the Fourier transform infrared spectrophotometer including:

a) accessory information reading means for reading accessory information provided to the accessory when the accessory is mounted in the sample chamber; and b) setting condition changing means for changing a setting condition for the interference optical system depending on the accessory based on the accessory information read by the accessory information reading means.

In the Fourier transform infrared spectrophotometer according to the present invention, each of plural types of accessories is provided with information for the accessory (accessory information). Then, the accessory information reading means reads the accessory information provided to the accessory when the accessory is mounted in the sample chamber. Based on the accessory information read as stated above, the setting condition changing means changes a setting condition for the interference optical system depending on the mounted accessory. Based on the setting condition changed as stated above, measurement is performed. Consequently, measurement can be performed with an optimum condition for each accessory.

The setting condition of the interference optical system for each accessory may be obtained after a preliminary test for measuring a background spectrum, and be recorded in recording means included in the Fourier transform infrared spectrophotometer for each accessory, and the setting condition changing means may read the setting condition corresponding to the accessory from the recording means. Instead of the recording means, the setting condition of the interference optical system for each accessory may be provided to the accessory as accessory information, which option is not included in the present invention.

For example, in the interference optical system in which infrared light is divided into two light beams, one of the light beams is reflected by the fixed mirror, the other light beam is reflected by the moving mirror and the two reflected light beams are then made to interfere with each other, the setting condition changing means changes a parameter for adjusting the direction of the fixed mirror relative to the moving mirror. When dynamic alignment is performed during measurement as stated above based on the parameter thus changed, in order to fix the direction of the fixed mirror relative to the moving mirror during movement of the moving mirror, feedback control is performed so that the parameter is maintained at a predetermined value for the relevant accessory, whereby the direction of the fixed mirror is continuously adjusted.

Also, the throughput is different depending on the accessory because of differences in optical path and optical elements, and thus, upon an accessory being mounted, the amount of infrared light received by a detector changes. In order to make up for the change, the setting condition changing means may change a parameter for setting a luminance of a light source.

The accessory information provided to each accessory may be recorded in ordinary readable recording means such as an IC chip or a bar code.

Advantageous Effects of Invention

The present invention enables provision of the FTIR that eliminates an effect of interference condition change depending on the relevant accessory mounted and enables high-accuracy measurement.

DESCRIPTION OF EMBODIMENTS

An embodiment of an FTIR according to the present invention will be described with reference to FIG. 1 to FIG. 6.

Embodiment (1) Configuration of FTIR of the Present Embodiment

Figure 1:
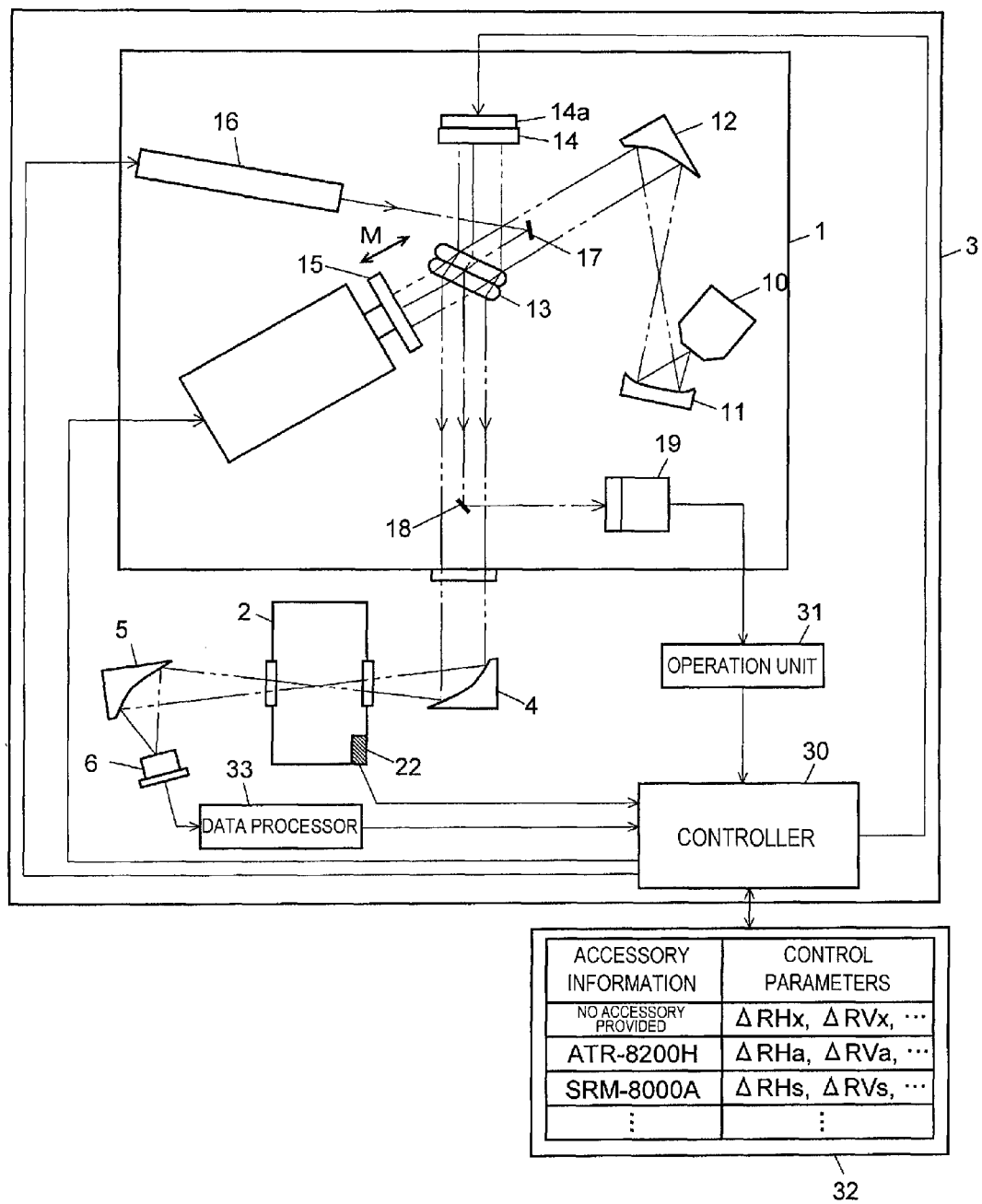
FIG. 1 is a diagram of a schematic configuration of an embodiment of an FTIR according to the present invention.

In the FTIR of the present embodiment, as illustrated in FIG. 1, an interferometer chamber 1 and a sample chamber 2 are provided on an upper surface of a base 3. Between the interferometer chamber 1 and the sample chamber 2, and the base 3, a suspension (not illustrated) is provided.

The interferometer chamber 1 is airtight, and a main interferometer including an infrared light source 10, a converging mirror 11, a collimating mirror 12, a beam splitter 13, a fixed mirror 14 and a moving mirror 15 is provided inside the interferometer chamber 1. Also, a control interferometer including a laser light source 16 and a laser mirror 17, and the beam splitter 13, the fixed mirror 14 and the moving mirror 15, which are shared with the main interferometer, is provided inside the interferometer chamber 1. The main interferometer generates main interference light to be cast to a sample, and the control interferometer measures parameters for adjusting the direction of the fixed mirror 14 relative to the moving mirror 15. A parabolic mirror 4, the sample chamber 2 (described above) and an ellipsoidal mirror 5 are arranged outside the interferometer chamber 1 in such a manner that main interference light emitted from the main interferometer is introduced to an infrared photodetector 6 through these components. A piezoelectric element 14a for adjusting the position (direction) of the fixed mirror 14 is provided on a back surface of the fixed mirror 14.

Figure 2:
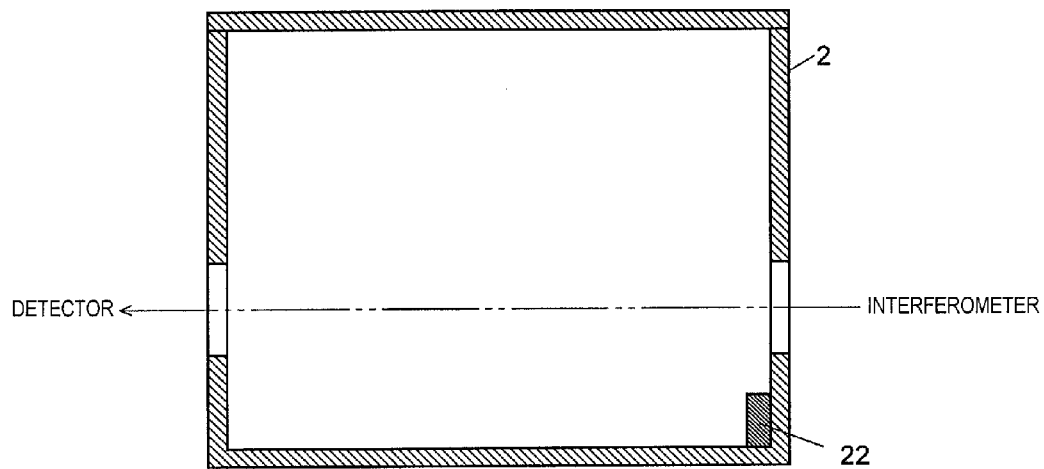
FIG. 2 is a diagram of a schematic configuration of a sample chamber in the FTIR of the present embodiment.
Figure 3:
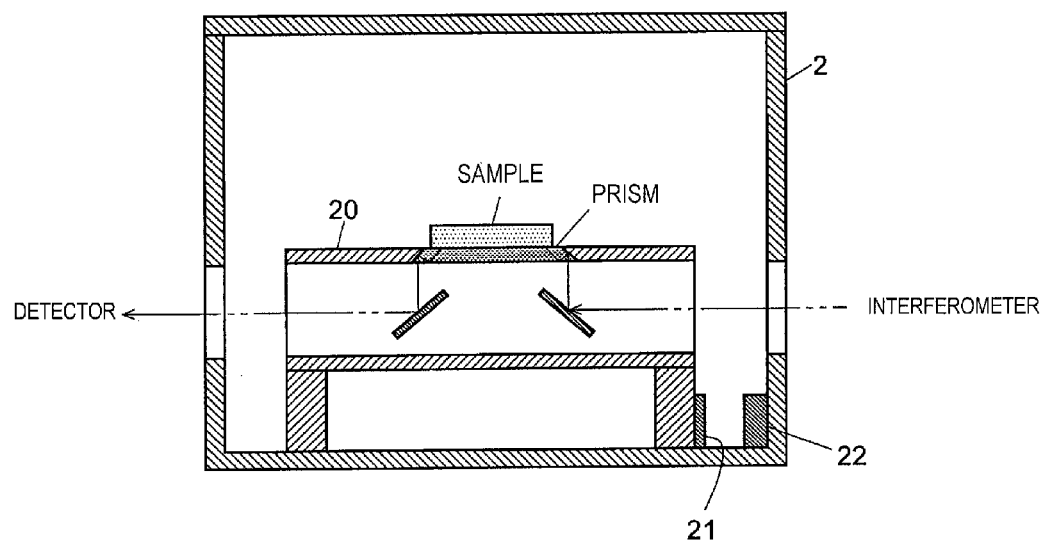
FIG. 3 is a schematic configuration diagram illustrating an example of an accessory mounted in the sample chamber in the FTIR of the present embodiment.
Figure 4:
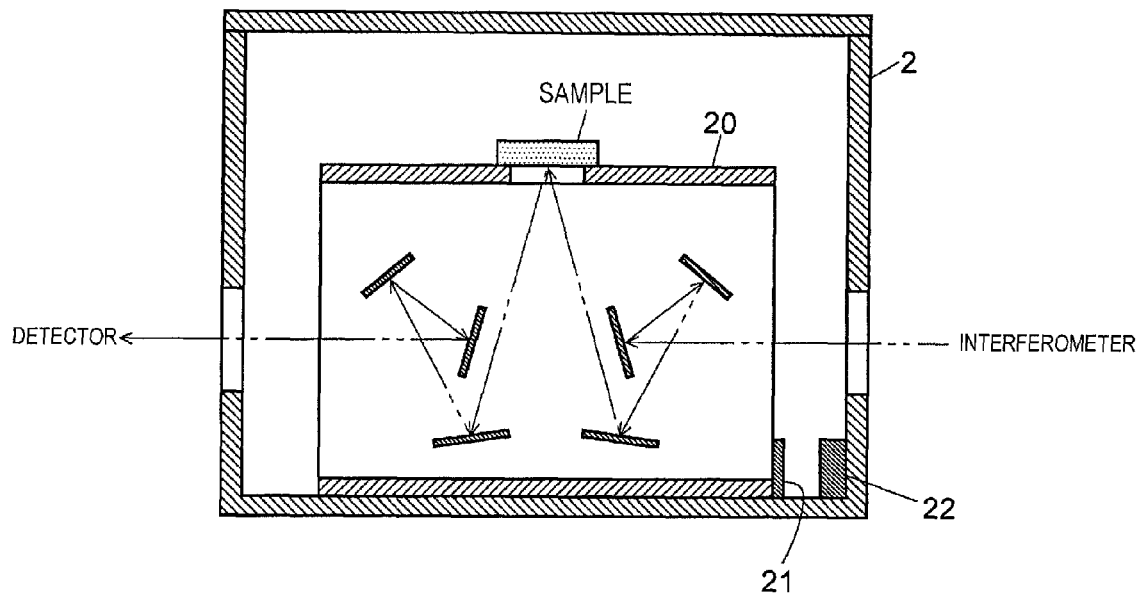
FIG. 4 is a schematic configuration diagram illustrating another example of an accessory mounted in the sample chamber in the FTIR of the present embodiment.
Figure 5:
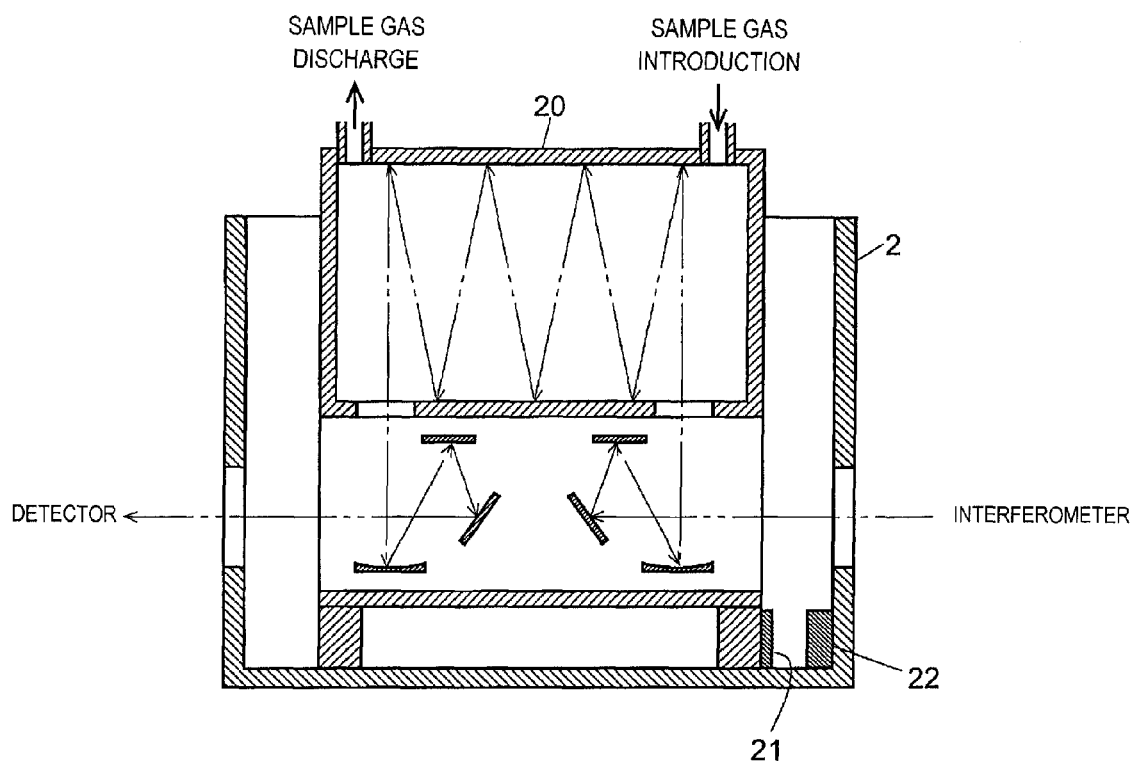
FIG. 5 is a schematic diagram illustrating another example of an accessory to be mounted in the sample chamber in the FTIR of the present embodiment.

FIG. 2 is a diagram of a schematic configuration of the sample chamber 2. An accessory 20 such as those in FIG. 3, FIG. 4 and FIG. 5 is mounted inside the sample chamber 2. The accessory 20 to be used in the FTIR according to the present embodiment is provided with an IC chip 21 with accessory information (for example, a product number) recorded. Also, an accessory information reading unit 22 is provided inside the sample chamber 2 to read the accessory information in the IC chip 21 when the accessory 20 is mounted in the sample chamber 2.

Also, a controller 30 (setting condition changing means) is provided in the FTIR of the present embodiment, and the controller 30 includes an operation unit 31, a parameter storage unit 32 and a data processor 33. Functions of the controller 30 will be described later in explanation of operation of the FTIR of the present embodiment.

Examples of the accessory 20 to be mounted in the sample chamber 2 include the following.

(a) Accessory According to Measurement Method (a-1) ATR Measurement Accessory

In ATR measurement, a sample is pressed against a prism, and an absorption spectrum of the sample is obtained from a slight amount of infrared light totally reflected from the inside of the sample while entering the inside of the sample at a boundary between the prism and the sample. As illustrated in FIG. 3, an ATR measurement accessory includes a prism to be pressed against a sample, and an optical system that makes the infrared light enter the sample at a predetermined angle and introduces the reflected light to a detector (for example, ATR-8200H manufactured by Shimadzu Corporation). Also, there is an ATR measurement accessory provided with a mechanism that moves the prism and the sample in order to change an angle of infrared light incident on the sample (for example, ATR-8000A manufactured by Shimadzu Corporation).

(a-2) Specular Reflection Measurement Accessory

Specular reflection measurement is a method in which a reflection spectrum of the sample is measured without using the prism, which has been employed before the ATR measurement. Also, in the specular reflection measurement method, the absorption spectrum can be obtained by subjecting the reflection spectrum to a Kramers-Krohig analysis. As illustrated in FIG. 4, a specular reflection measurement accessory includes an optical system that makes infrared light enter the sample at a predetermined angle and introduces reflected light to a detector (for example, SRM-8000A manufactured by Shimadzu Corporation). Among specular reflection measurement accessories, also, there are those provided with a mechanism that changes an angle of the infrared light incident on the sample (for example, VeeMAX II A manufactured by Shimadzu Corporation).

(a-3) Transmission Measurement Accessory

Transmission measurement is literally a method in which a spectrum of infrared light transmitted by the sample is measured. A transmission measurement accessory includes a sample holder provided with a window formed of a hole or a material that transmits the infrared light in order to prevent the infrared light transmitted by the sample from being blocked, and an optical system that causes the infrared light to transmit the sample and introduces the infrared light to a detector.

(b) Accessories According to State of Sample (b-1) Liquid Cell

A liquid cell is used when a liquid sample is measured. Also, separately from a liquid cell to be used for a nonvolatile liquid sample, a more highly-airtight liquid cell is used for a volatile liquid sample.

(b-2) Gas Cell

A gas cell is used when a gas sample is measured. Also, when a rarefied gas sample is measured, as illustrated in FIG. 5, the gas cell provided with a reflection mirror that repeatedly reflects the infrared light inside the cell is used in order to increase an amount of absorption of the infrared light by the sample.

(c) Infrared Microscope

Use of the FTIR in combination with an infrared microscope enables an enlarged image of the sample and a sample spectrum to be obtained simultaneously. The infrared microscope, as the accessory for the FTIR, generally includes an optical system as a microscope that includes an objective lens facing the sample, and an optical system as the FTIR which causes infrared light from a side of the sample to enter the sample and extracts reflected light from an opposite side of the sample.

(2) Operation of FTIR in Present Embodiment (2-1) Preliminary Measurement

In the FTIR, normally, at the time of shipment or maintenance, an interference optical system is set so as to be optimum with no accessory mounted in the sample chamber. The same applies to the present embodiment. Here, accessories to be mounted in the sample chamber 2 are different in weight from one another, and thus, distortion occurring in the base 3 supporting the interferometer chamber 1 and the sample chamber 2 is also different depending on the accessory. For the difference in distortion of the base 3, a parameter for adjusting an inclination of the fixed mirror 14 in a dynamic alignment is required to change depending on the accessory. Therefore, in a state in which the interference optical system is set in advance to be optimum with no accessory mounted in the sample chamber, preliminary measurement for determining the parameter is performed for each accessory, with the accessory mounted in the sample chamber. The preliminary measurement may be performed at the time of factory shipping or may be performed by a user when a new accessory is mounted for the first time. A method of the preliminary measurement will be described below.

First, the accessory is mounted in the sample chamber 2. Then, laser light is emitted from the laser light source 16 in the control interferometer. The laser light is cast to the beam splitter 13 via the laser mirror 17 and thereby divided into two laser light beams. One of the laser light beams is reflected by the fixed mirror 14 and returns to the beam splitter 13, and the other laser light beam is reflected by the moving mirror 15 and returns to the beam splitter 13. Consequently, laser interference light resulting from interference of these two light beams is generated and sent to an exit of the interferometer chamber 1, that is, in the direction toward the parabolic mirror 4. The laser interference light advances in the form of a light flux having a very small diameter, and is thus reflected by a laser mirror 18 inserted in the optical path and is then introduced to a laser detector 19.

The laser detector 19 is a quadrant photodiode whose light reception surface is divided in quarters by two axes perpendicular to each other, and signals obtained by four light reception units are output in parallel. The respective signals obtained by the four light reception units are input to the operation unit 31. Based on a reference signal Sr obtained from one light reception unit among the four light reception units, and a horizontal signal Sh and a vertical signal Sv obtained respectively by light reception units horizontally and vertically adjacent to the light reception unit from which the reference signal Sr has been obtained, the operation unit 31 calculates a phase difference $\Delta RH$ between the reference signal Sr and the horizontal signal Sh, and a phase difference $\Delta RV$ between the reference signal Sr and the vertical signal Sv. The phase differences ΔRH and ΔRV obtained here are provisional parameters ΔRH0 and ΔRV0.

Next, infrared light is emitted from the infrared light source 10. The infrared light is introduced to the beam splitter 13 via the converging mirror 11 and the collimating mirror 12 and thereby divided into two light infrared beams. One of the infrared light beams is reflected by the fixed mirror 14 and returns to the beam splitter 13, and the other infrared light beams is reflected by the moving mirror 15 and returns to the beam splitter 13. Consequently, main interference light resulting from interference of these two light beams is generated. The main interference light is detected by the infrared photodetector 6 via the parabolic mirror 4, the sample chamber 2 and the ellipsoidal mirror 5. Then, the detection of the infrared light is performed while the moving mirror 15 is moved, whereby the controller 30 obtains an interferogram, and the controller 30 subjects the interferogram into a Fourier transform to obtain a power spectrum with the wavenumber as an abscissa and the intensity as an ordinate. Also, throughout the entire length of the movement of the moving mirror 15, the controller 30 calculates the phase differences ΔRH and ΔRV based on the signals from the laser detector 19, and performs feedback control of a voltage applied to the piezoelectric element 14a so as to maintain these phase differences ΔRH and ΔRV at the provisional parameters ΔRH0 and ΔRV0, thereby adjusting the inclination of the fixed mirror 14.

The controller 30 performs a Fourier transform of the interferogram thus obtained to obtain a power spectrum with the wavenumber as an abscissa and the intensity as an ordinate. The controller 30 calculates intensities at arbitrary wavenumbers (for example, three points, 1000 $cm^{-1}$, 2000 $cm^{-1}$ and 3000 $cm^{-1}$) of the power spectrum. If each of the intensities is a predetermined value or more, the provisional parameters ΔRH0 and ΔRV0 are set as parameters ΔRHa and ΔRVa for adjusting the inclination of the fixed mirror 14 in dynamic alignment. On the other hand, if each of the intensities is less than the predetermined value, an operation of obtaining a power spectrum as described above after changing the provisional parameter(s) ΔRH0 and/or ΔRV0 is repeated until each of the intensities of the power spectrum become the predetermined value or more, and the provisional parameters ΔRH0 and ΔRV0 when each of the intensities becomes the predetermined value or more are set as the parameters ΔRHa and ΔRVa.

The parameters ΔRHa and ΔRVa thus obtained is stored in the parameter storage unit 32 as a parameter table in association with information of the accessory mounted in the sample chamber 2. These numerical values serve as information to be used when a setting condition for the interference optical system is changed during measurement of the sample as described below.

(2-2) Measurement of Sample

First, a user mounts the accessory 20 according to the purpose of the measurement in the sample chamber 2. Consequently, the accessory information recorded in the IC chip 21 of the accessory 20 is read by the accessory information reading unit 22 arranged in the sample chamber 2 and send to the controller 30. Upon receipt of the accessory information from the accessory information reading unit 22, the controller 30 obtains parameters ΔRHa and ΔRVa for the accessory mounted in the sample chamber 2 with reference to the parameter table in the parameter storage unit 32. Next, the user sets a sample in the sample chamber 2 and performs an operation to make the FTIR device start a measurement.

Upon the start of the measurement, an interferogram is obtained by a method similar to that of the preliminary measurement, and the interferogram is subjected to a Fourier transform, whereby a power spectrum is obtained. The power spectrum obtained here is a sample spectrum including information of the sample because main interference light is transmitted or reflected by the sample when the main interference light passes through the sample chamber 2. Then, during movement of the moving mirror 15, the inclination of the fixed mirror 14 is adjusted based on the parameters ΔRHa and ΔRVa. Since these parameters ΔRHa and ΔRVa are set for each accessory 20, an intense sample spectrum can be obtained without being affected due to a variety of distortion of the base 3 depending on the accessory 20.

(2-3) Change of Settings for Parameters

Optimum values of the parameters may vary due to factors other than the weight of the accessory such as aging deterioration of the device, measurement environment change or optical axis displacement. In order to respond to such variation, a user of the device, or staff of a company who performs periodic maintenance of the device, may re-adjust the settings for the parameters as described below.

Figure 6:
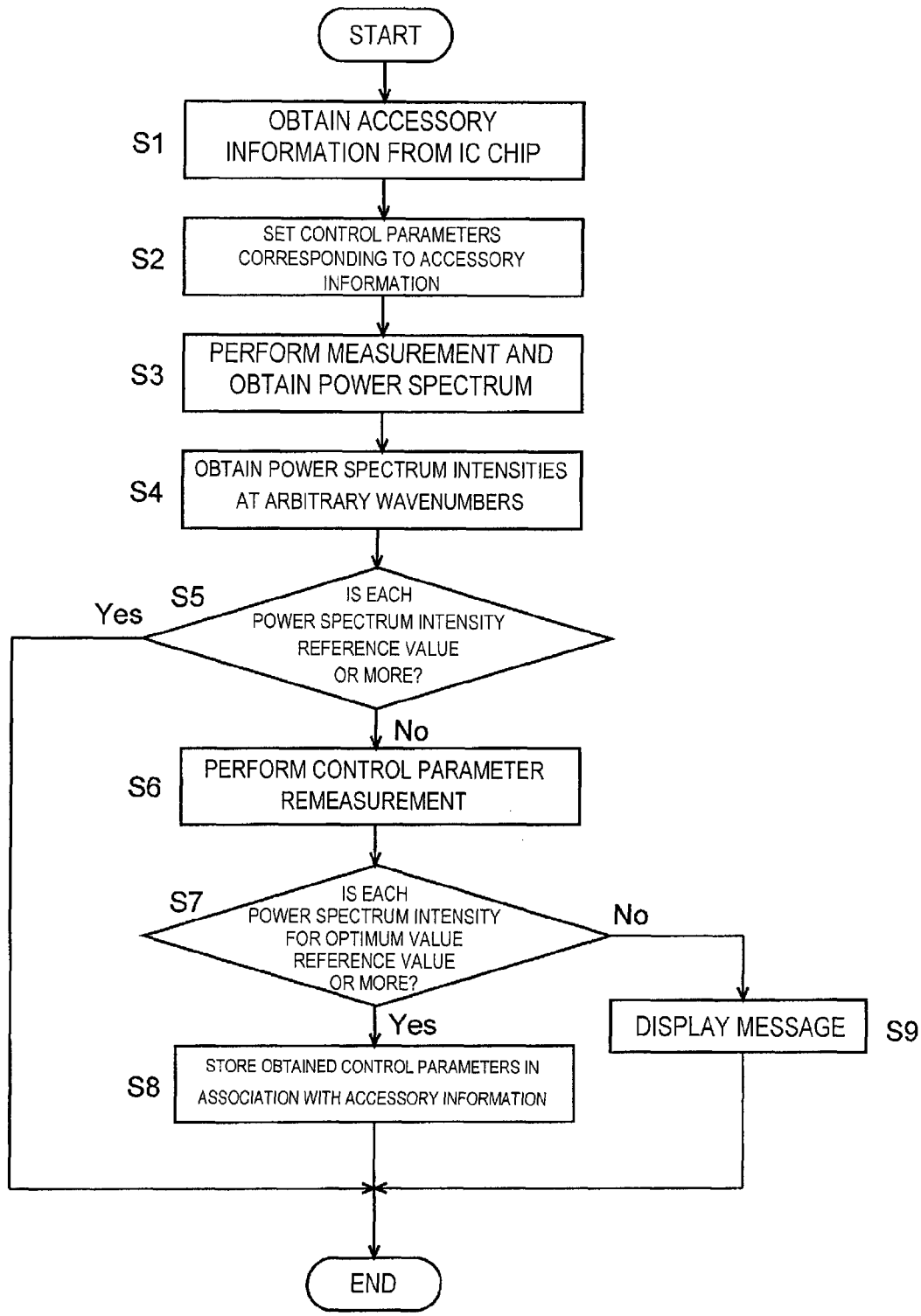
FIG. 6 is a flowchart of a process for re-adjusting an optimum value of a phase difference in dynamic alignment based on a power spectrum obtained by measurement in the FTIR of the present embodiment.

FIG. 6 is a flowchart illustrating a process by the controller 30 of re-adjusting parameters ΔRHa and ΔRVa based on a power spectrum obtained by a measurement. First, a power spectrum is obtained by performing an operation that is similar to that of normal sample measurement using the parameters ΔRHa and ΔRVa with no sample mounted in the sample chamber 2 (step S1 to S3). The controller 30 obtains intensities at arbitrary wavenumbers of the obtained power spectrum (step S4). Then, the controller 30 determines whether or not each of the intensities is the reference value or more (step S5). If each of the intensities is the reference value or more, it is determined that a sufficiently-high power spectrum has been obtained, and the measurement ends. On the other hand, if each of the intensities is smaller than the reference value, as in the preliminary measurement described above, parameter remeasurement is performed to obtain parameters that provide intensities of the power spectrum each of which is the predetermined value or more by repeating the operation of obtaining a power spectrum as described above after changing the parameters (step S6). Then, if such parameters are obtained, the process proceeds from step S7 to step S8, and the obtained parameters are stored in association with the relevant accessory information (step S8). On the other hand, if such parameters are not obtained, there may be a problem in the accessory 20 itself (for example, in an optical axis in the accessory 20 that is determined by mirrors included in the accessory 20), and the process proceeds from step S7 to step S9, and a message indicating that adjustment or the like of the accessory 20 is necessary is displayed.

Although the above embodiment has been described in terms of an example in which phase differences are used as parameters, for example, a luminance of the infrared light source 10 can be used as a parameter. Because the throughput differs depending on the accessory and the amount of infrared light received by a detector varies when the accessory is mounted, resultant power spectrum intensity. Thus, the luminance for the infrared light source 10 is changed according to the type of the accessory 20 so that a power spectrum intensity that is the same as that when no accessory is mounted is obtained. Also, since the luminance for the infrared light source 10 is proportional to electric power supplied to the infrared light source 10, a value of the electric power may be stored as a parameter, for each accessory.

REFERENCE SIGNS LIST

10 . . . Infrared Light Source
11 . . . Converging Mirror
12 . . . Collimating Mirror
13 . . . Sample Chamber
14 . . . Fixed Mirror
14a . . . Piezoelectric Element
15 . . . Moving Mirror
16 . . . Laser Light Source
17, 18 . . . Laser Minor
19 . . . Laser Detector
2 . . . Sample Chamber
20 . . . Accessory
21 . . . IC Chip
22 . . . Accessory Information Reading Unit
3 . . . Base
30 . . . Controller
31 . . . Operation Unit
32 . . . Parameter Storage Unit
33 . . . Data Processor
4 . . . Parabolic Minor
5 . . . Ellipsoidal Mirror
6 . . . Infrared Photodetector

The invention claimed is:

1. A Fourier transform infrared spectrophotometer comprising:
   a) a sample chamber,
   b) an accessory detachably installed in the sample chamber to which accessory information representing a type of the accessory is provided,
   c) an interference optical system,
   d) a common base on which the sample chamber and the interference optical system are mounted;
   e) an accessory information reader for reading the accessory information when the accessory is mounted in the sample chamber; and
   f) a setting condition changer having a parameter table for changing a setting condition for the interference optical system depending on the accessory based on the accessory information read by the accessory information reader.

2. The Fourier transform infrared spectrophotometer according to claim 1, wherein the setting condition is a parameter for adjusting a direction of a fixed mirror relative to a moving mirror in the interference optical system in which infrared light is divided into two light beams, one of the light beams is reflected by the fixed mirror and the other light beam is reflected by the moving mirror, and the two reflected light beams are then made to interfere with each other.

3. The Fourier transform infrared spectrophotometer according to claim 2, wherein the setting condition is a parameter for setting a luminance of a light source of infrared light to be cast to the sample.

4. The Fourier transform infrared spectrophotometer according to claim 1, wherein the setting condition is a parameter for setting a luminance of a light source of infrared light to be cast to the sample.

* * * * *